(12) United States Patent
You et al.

(10) Patent No.: US 6,295,864 B1
(45) Date of Patent: Oct. 2, 2001

(54) ANALYSIS SYSTEM AND METHOD FOR WATER-SOLUBLE CONTAMINANTS IN A CLEANROOM ENVIRONMENT

(75) Inventors: Nam-hee You; Soon-young Lee; Jung-sung Hwang, all of Yongin; Kwang-young Kim, Yusung-gu, all of (KR)

(73) Assignee: Samsung Electronics Co., Ltd., Suwon (KR)

( * ) Notice: Subject to any disclaimer, the term of this patent is extended or adjusted under 35 U.S.C. 154(b) by 0 days.

(21) Appl. No.: 09/236,545

(22) Filed: Jan. 26, 1999

(30) Foreign Application Priority Data

Mar. 27, 1998 (KR) .................................................. 98-10819

(51) Int. Cl.$^7$ .................................................. G01N 11/00
(52) U.S. Cl. ...................... 73/53.01; 73/61.52; 73/61.55; 73/863.12; 73/31.02; 422/82.04
(58) Field of Search ............................... 73/53.01, 53.07, 73/61.52, 61.71, 61.55, 61.41, 863.12, 23.2, 31.01, 31.03, 31.07; 95/87; 436/181; 422/82.02, 82.04; 324/691, 693; 34/722

(56) References Cited

U.S. PATENT DOCUMENTS

| | | | | |
|---|---|---|---|---|
| 3,556,950 | * | 1/1971 | Dahms | 422/82.04 |
| 4,530,250 | * | 7/1985 | Gay et al. | 73/863.12 |
| 4,861,555 | * | 8/1989 | Mowery, Jr. | 73/61.52 |
| 5,141,531 | * | 8/1992 | Parrish | 95/126 |
| 5,428,964 | * | 7/1995 | Lobdell | 73/31.02 |
| 5,643,457 | * | 7/1997 | Abramov et al. | 210/668 |
| 5,725,634 | * | 3/1998 | Takasuga et al. | 95/45 |
| 5,762,763 | * | 6/1998 | Tsargorodski | 203/11 |
| 5,855,652 | * | 1/1999 | Talley | 96/44 |

* cited by examiner

Primary Examiner—Daniel S. Larkin
Assistant Examiner—Michael Cygan

(57) ABSTRACT

An analysis system and method for a cleanroom environment is disclosed wherein on-line testing of water-soluble contaminants is performed by condensing water vapor from an air sample taken from the clean room. The condenser is connected to a analyzing unit that is used to measure and analyze the water-soluble contaminants in the condensed water received from the condensing unit.

33 Claims, 4 Drawing Sheets

ANALYSIS SYSTEM AND METHOD FOR WATER-SOLUBLE CONTAMINANTS IN A CLEANROOM ENVIRONMENT

BACKGROUND OF THE INVENTION

The present invention relates to a clean room environment analysis system and to an analysis method using same. More particularly, the present invention relates to a system for analyzing water-soluble contaminants present in the air of a clean room.

It is well known that the quality and yield of semiconductor devices are greatly affected by the ambient conditions under which they are manufactured. Accordingly, manufacturing processes for semiconductor devices are performed in cleanrooms having highly-purified environments in which various kinds of air contaminants, such as dust, microscopic organisms, ion particles, etc., must be eliminated to the greatest, practical degree possible. This is especially true for those clean room fabrication processes which form highly-sophisticated patterns on semiconductor devices. Unfortunately, in actual practice, the air in cleanrooms always contains some contaminants, and these contaminants create wafer defects. Thus, techniques for controlling air quality in cleanrooms have become increasingly important as semiconductor geometries have become increasingly small.

Water-soluble contaminants, such as ammonia, nitric acid compounds, sulfuric acid compounds and the like, are particularly troublesome. These water-soluble contaminants are generated when various semiconductor compounds, gases, or other contamination sources come into contact with moisture in the air. These contaminants typically have ionic bonds, and are thus easily attached to the surface of a semiconductor device under manufacture. Water-soluble contaminants, along with other contaminants, create a "haze" phenomenon over the surface of a semiconductor wafer. Haze causes deterioration in photoresist layers, and during diffusion processes may act as undesired dopants.

As a result of these problems, which are merely selected examples, various conventional analysis systems and methods for analyzing water-soluble contaminants found in clean room air have been developed in previous attempts to control water-soluble contaminants. One widely used method is the "Jar Test." In the Jar test, a jar filled with deionized water is left in the clean room. Over time, particles are absorbed into the deionized water. Subsequently, the "contaminated" deionized water is analyzed to roughly determine the nature and content of clean room contaminants. Another conventional method is the "Impinger Method," in which some portion of the clean room air is forcibly circulated and passed through deionized water. As with the Jar Test, the resulting contaminated water may be evaluated.

These conventional methods for capturing water soluble contaminants are simple and easily employed. Unfortunately, it takes a long time for sufficient contamination particles to be captured for evaluation. The length of time required to capture sufficient water-soluble contaminants in conventional methods creates evaluation inaccuracies. Further, contamination evaluation is done after-the-fact, rather than in real-time. This precludes the identification of transient clean room contamination phenomenon, the accurate development of short-term evaluation criteria, and the recognition of absolute contaminant concentration relationships with other factors such a time.

SUMMARY OF THE INVENTION

The present invention is directed to a clean room environment analysis system and method for using same which substantially overcomes one or more of the problems associated with conventional systems and methods. The present invention provides an analysis system and method for a clean room environment which reduces the time required to capture air-bourne, water-soluble contaminants. Analysis efficiency and accuracy are improved. The present invention provides essentially real-time or "On-line" analysis capabilities. The present invention also provides an analysis system and method for a clean room environment which allows distinction between various kinds of contaminants, as well as absolute measurement of various water-soluble contaminant concentrations.

To achieve these and other advantages, the present invention provides an environment analysis system for a clean room comprising: a cooling unit condensing water having water-soluble contaminants therein from water vapor contained in an air sample extracted from the clean room, and an analyzing unit analyzing the condensed water received from the condensing unit. The cooling unit comprises; a condenser through which the air sample passes, such that water vapor from the air sample condenses within the condenser, cooling means for cooling the condenser, a vacuum pressure generator forcing the air sample through the condenser, a condensed water collector receiving the condensed water from the condenser, and a condensed water supplier supplying condensed water from the condensed water collector to the analyzing unit.

The condenser preferably comprises at least one condensing tube vertically installed such that the air sample is induced at a top of the condenser and travels downwardly from the top to be discharged at a bottom of the condenser, wherein the at least one condensing tube is installed to pass through the cooling means.

More particularly, the condenser comprises a plurality of parallel condensing tubes made from glass.

The cooling means comprises; a cooling tank containing a cooling fluid in contact with the condenser; and a cooler comprising a compressor, an expander, and means for defining a cooling cycle such that a cooling medium circulates between the compressor and the expander.

The cooling tank further comprises a front door assembly, such that when the front door assembly is opened, the condenser may be removed from the cooling tank. Further, the means for defining a cooling cycle comprises a controller driving the compressor, such that an inner wall temperature of the condenser maintains a temperature within a range of from 0° C. to 10° C.

The vacuum pressure generator comprises: an air suction pipe installed with one end extending into a bottom end of the at least one condensing tube, and a vacuum pump attached to another end of the air suction pipe drawing the air sample through the condensing tube. One end of the air suction pipe is inserted into the bottom end of the at least one condensing tube and is separated from the inner wall of the condensing tube. The vacuum pressure generator further comprises a mass flow controller connected to the air suction pipe and defining the volume of the air sample amount drawn through the condenser.

The condensed water collector comprises: a condensed water vessel having a funnel-shape installed beneath the condenser to capture condensed water from the condenser, and a condensed water pipe transporting condensed water collected in the condensed water vessel to the analyzing unit. Further, the condensed water collector comprises a valve installed in the condensed water pipe, and a controller selectively opening and closing the valves by application of a control signal.

In one aspect, the condensed water collector comprises: a plurality of condensed water vessels, each having a funnel-shape, and each being installed beneath a respective condensing tube to capture condensed water from the respective condensing tube, a condensed water pipe transporting condensed water collected in each of plurality of condensed water vessels to the analyzing unit, a controller; and a plurality of valves fitted into the condensed water pipe, wherein the controller selectively opens and closes each one of the plurality of valves, wherein each one of the plurality of valves is respectively associated with one of the plurality of condensing tubes, such that selective opening and closing of each one of the plurality of valves defines the transport of condensed water from the associated one of the plurality of condensing tubes to the analyzing unit. Each one of the plurality of valves is preferably a solenoid valve.

The condensed water supplier further comprises: an injector loop installed along the condensed water pipe, wherein the condensed water collected in the condensed water vessel is temporarily accumulated in the injector loop before being supplied to the analyzing unit; and a fluid pump providing pressure to the condensed water accumulated in the injector loop. The fluid pump is a positive displacement syringe pump having a pump capacity of from 0.1 to 2 ml per minute.

Further, the condensed water supplier may include a discharge line for directly discharging the condensed water accumulated in the injector loop without passing through the analyzing unit. The discharge line comprises a condensed water discharge pipe installed at an outlet of the fluid pump and directly discharging the condensed water accumulated in the injector loop without passing through the analyzing unit, and a discharged water container receiving the condensed water from the condensed water discharge pipe. The discharged water container may include a level sensor sensing the amount of condensed water in the discharge water container, and a controller defining a discharge time for the condensed water discharged through the condensed water discharge pipe in response to a signal from the level sensor.

The analyzing unit is an ion chromatography device: comprising; a solvent supplier mixing a solvent with condensed water to form a test sample, a column receiving the test sample and ion-separating the test sample into specific material groups, a suppressor for suppressing the conductivity of the solvent in the test sample among the specific material groups separated in the column, a conductivity meter analyzing the test sample by measuring conductivity of the specific material groups, and a discharge line for discharging the test sample passing through the conductivity meter.

The solvent supplier comprises a solvent supply source for containing the solvent, and a solvent supply pump transporting the solvent from the solvent supply source to the inject loop. Additionally, the ion chromatography may include a standard solution supplier for supplying a standard solution of ions to the conductivity meter in order to obtain initialization data for the conductivity meter, and the conductivity meter of the analyzing unit comprises a user defined functional tool adapted to calculate the concentration of water-soluble contaminants in the air sample as a product of measured values.

Finally: the analysis system may comprise; a particle counter for counting particles contained in the air sample, a hygrometer for measuring the humidity of the air sample, a thermometer for measuring the temperature of the air sample, and a pressure gauge for measuring the pressure of the air sample.

In another aspect: the analysis system for cleanroom environment comprises; a condensing unit condensing water vapor containing water-soluble contaminants from an air sample taken from the cleanroom, an analyzing unit analyzing the condensed water received from the condensing unit, and a condensed water supply unit transporting condensed water from the condensing unit to the analyzing unit.

The condensed water supply unit comprises a condensed water pipe having one end connected to the condensing unit and another end connected to the analyzing unit, an injector loop connected along the condensed water pipe to temporarily accumulate condensed water, and a syringe pump applying pressure to the condensed water accumulated in the injector loop to supply the condensed water to the analyzing unit.

In yet another aspect, the present invention provides an analysis method for a cleanroom environment, comprising the steps of: providing an air sample taken from the cleanroom, cooling the air sample to produce condensed water containing water-soluble contaminants present in the air sample, and supplying the condensed water to an analyzing unit. The step of cooling the air sample comprises the steps of drawing the air sample through a condenser by means of a vacuum pump, and operating the condenser to cool the air sample using a circulated cooling medium. Further, the step of drawing the air sample through a condenser comprises the step of controlling the drawing velocity of the air sample such that air sample is optimally cooled to produce the condensed water before the air sample is discharged from the condenser.

The analysis method may further comprise the step of mixing a solvent with at least a portion of the condensed water to form a test sample, and providing the test sample to the analyzing unit. Prior to the step of cooling the air sample, a step of cleaning the condenser using condensed water as cleaning water in order to remove water existing inside condenser without passing the cleaning water through the analyzing unit may be performed.

BRIEF DESCRIPTION OF THE DRAWINGS

The present invention will be understood following a review of the description of the preferred embodiment(s) below with reference to the accompanying drawings in which.

DETAILED DESCRIPTION OF THE PREFERRED EMBODIMENTS

Figure 1:
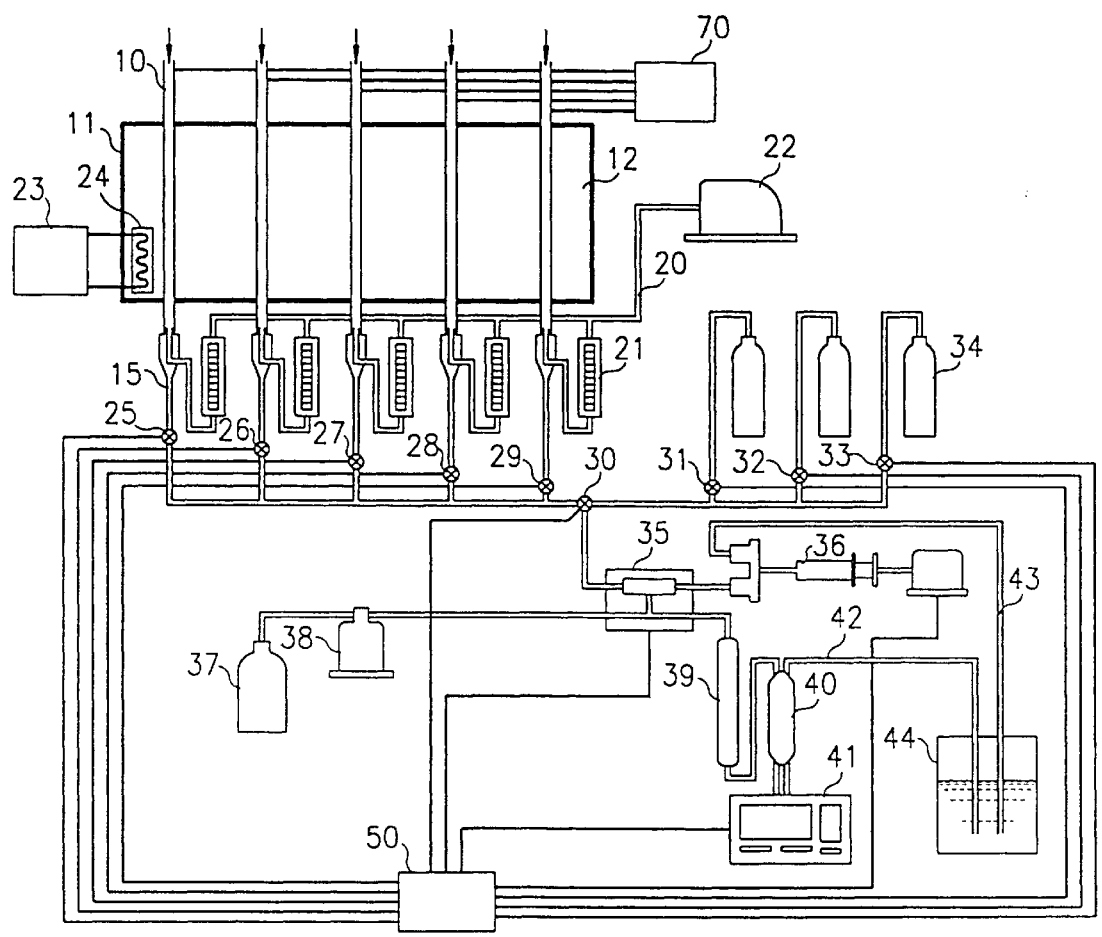
FIG. 1 shows a cleanroom environment analysis system according to an embodiment of the present invention.

Reference will now be made to a preferred embodiment of the present invention, illustrated in the accompanying drawings. Referring to FIG. 1, the cleanroom environment analysis system of the present invention comprises a cooling unit and an analyzing unit. The cooling unit condenses water from water vapor found in a reference air sample taken from the cleanroom.

The analyzing unit detects and analyzes water-soluble contaminants contained in the condensed water received from the cooling unit. In addition, the analyzing unit displays the results of its analysis and writes the results to a database. The analyzing unit may be an ion-chromatographer which ionizes the water-soluble contaminants contained in the condensed water, divides the contaminants into specific groups, and measures the conductivity of each group so as to analyze the nature of each group.

As shown in FIG. 1, the cooling unit comprises a condenser, here a plurality of parallel arranged condensing tubes 10 which receive a reference air sample to be analyzed from the cleanroom. As the air sample passes through condensing tubes 10 water vapor contained in air sample cools and condenses on the inner walls of condensing tubes 10. Five condensing tubes are shown in present embodiment, but one of ordinary skill will appreciate that any practical number of condensing tubes may be used.

The cooling unit further comprises: cooling means for cooling condensing tubes 10, a vacuum pressure generator forcing the reference air sample through condensing tubes 10, a condensed water collector collecting the condensed water, and a condensed water supplier supplying the condensed water to the analyzing unit.

Preferably, condensing tubes 10 are constructed such that the condensed water can be easily collected. In the preferred embodiment, condensing tubes 10 are vertically installed such that the air sample is induced into a top of each condensing tube, the air sample flows downwardly through each condensing tube, and is then discharged through a bottom. Condensing tubes 10 can be made of various types of materials, but a transparent material is preferred so that a system operator may examine tube contents. "Pyrex," a trademark of Coming Corporation for a family of glass products, and similar glass products containing boron-silicic acid are preferably used because of their chemical resistance and heat resistance.

The cooling means may take many forms; for example, gas may be blown over the condenser, the condenser may be placed next to a cooling structure, or placed in a fluid or gas tank structures. In the present embodiment, the cooling means comprises a sealed cooling tank 11 containing a cooling fluid 12 surrounding condensing tubes 10, and a cooler for controlling the temperature of cooling fluid 12.

The cooler preferably comprises a compressor 23 and expander 24. These two elements cooperate in well known fashion with a cooling medium to cool cooling fluid 12 within cooling tank 11 and thus maintain a desired temperature for cooling fluid 12. The cooler is thus a conventional refrigerator having a defined cooling cycle such that the cooling medium circulates between compressor 23 and expander 24.

Water may be used as cooling fluid 12, but cooled water is difficult to manage, and has low heat conductivity which is often inadequate for use as cooling fluid 12. In view this, a specific gas, gas mixture—like air, or some other liquid may be used in place of water as cooling fluid 12.

Figure 2:
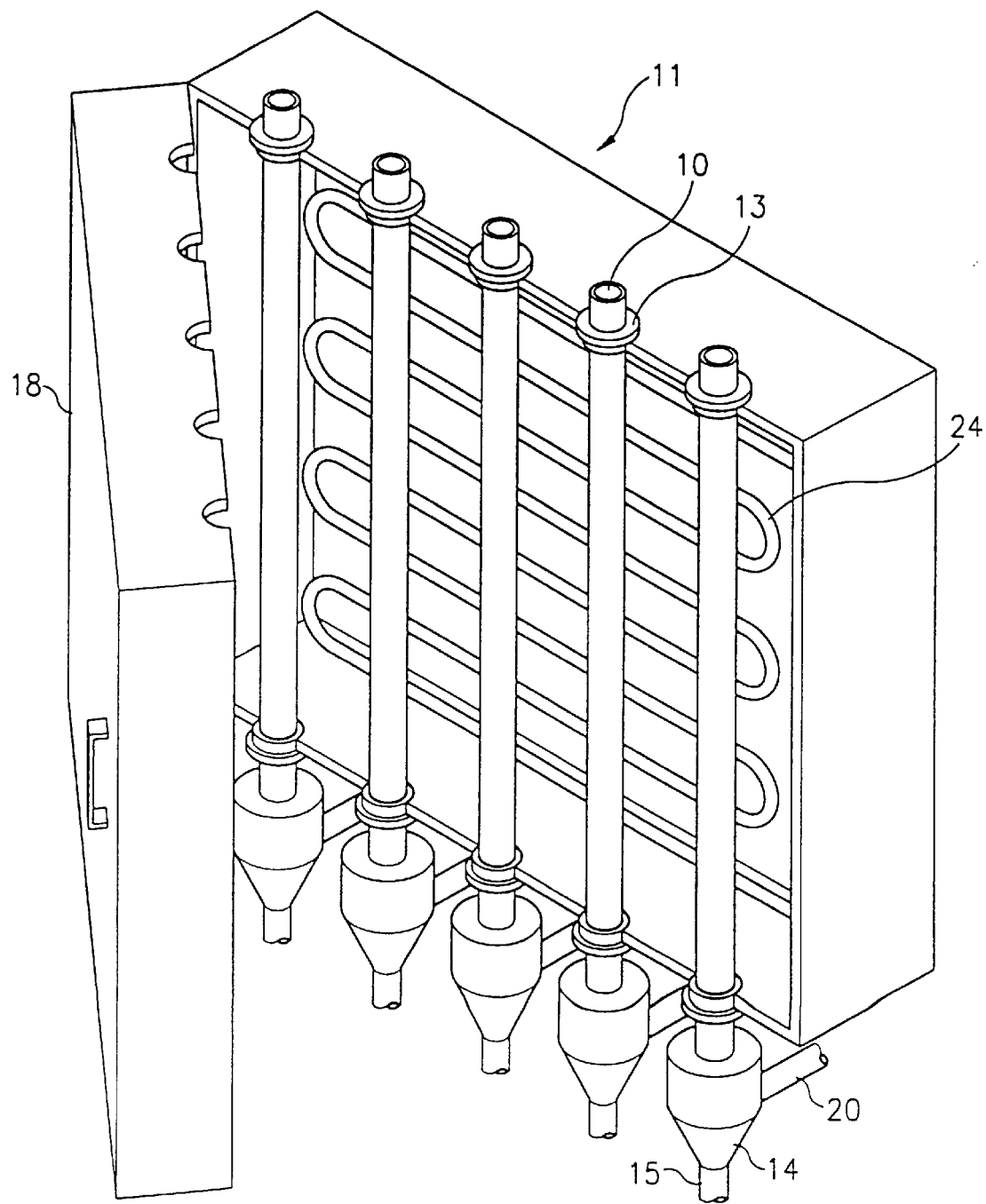
FIG. 2 is a perspective view of a cooling tank shown in FIG. 1.

Cooling tank 11 is constructed, as shown in FIG. 2, in such a manner that the expander 24 is installed on one inner wall of cooling tank 11. A door assembly 18 opening/closing the front of cooling tank 11 over the condenser is provided. When open, door assembly 18 allows easy removal of the condenser. A plurality if openings are formed in the top and bottom of cooling tank 11. The plurality of openings define a space into which condensing tubes 10 are vertically installed in cooling tank 11. With these openings formed at the juncture of front door assembly 18 and a back portion of cooling tank 11, condensing tubes 10 are fixed in cooling tank 11. A packing member 13 is provided in each opening to seal and secure a respective condensing tube. Packing member 13 thus supports each condensing tube by applying a compressive force on the condensing tube when door assembly 18 is closed, and seals the cooling fluid within cooling tank 11. Packing member 13 is preferably made of rubber having a good elasticity.

The cooler also includes a controller (not shown) for controlling compressor 23 to maintains a desired condensation temperature, preferably in a range of from 0° C. to 10° C., but at a temperature at which the condensed water will not freeze in the condensing tube.

As shown in FIG. 1, the vacuum pressure generator includes an air suction pipe, a vacuum pump, and a Mass Flow Controller. Air suction pipe 20 is installed with one end inserting into a bottom end of each one of condensing tubes 10 and pulls the air sample through the condensing tube. Vacuum pump 22 is connected to the other end of air suction pipe 20 to create a vacuum pressure in air suction pipe 20. A mass flow controller (MFC) 21 is placed in respective sections of air suction pipe 20, each section corresponding to a condensing tube, and regulates the flow of the air sample into air suction pipe 20.

Figure 3:
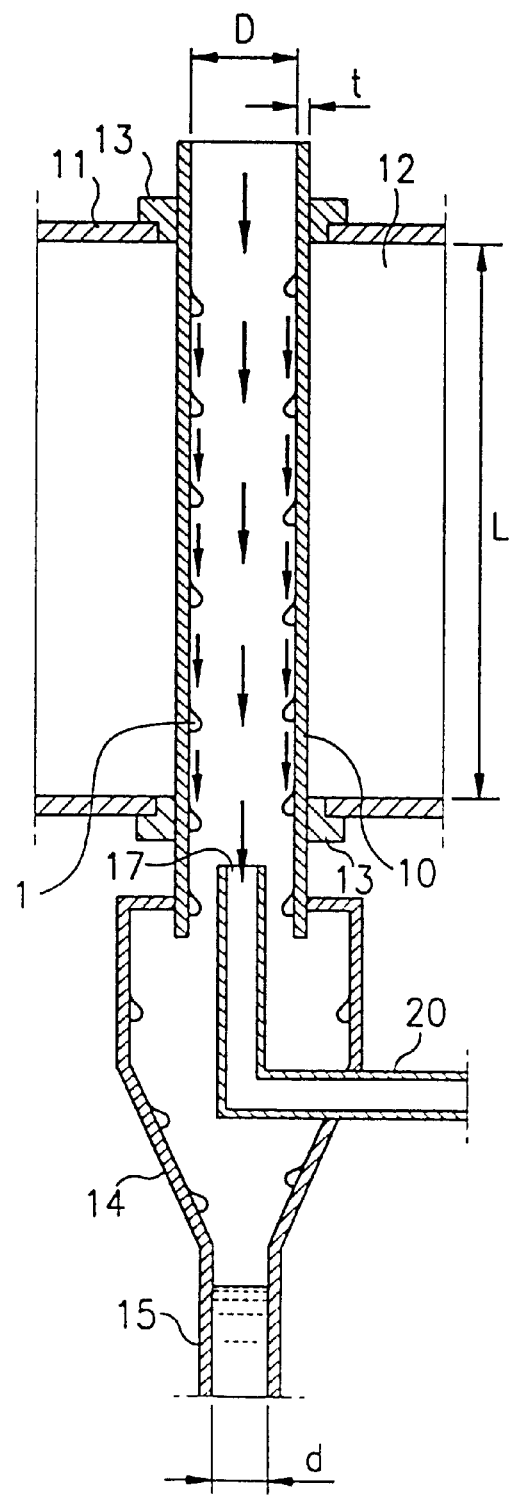
FIG. 3 is a cross-sectional side-view showing a condensing tube shown in FIG. 1.

As shown in greater detail in FIG. 3, one end of air suction pipe 20, the air inlet end 17, is fitted into the bottom end of condensing tube 10 such that air suction pipe 20 does not touch the inner wall of condensing tube 10 in order to prevent condensed water 1 dripping down the inner wall from entering suction pipe 20. Down air suction pipe 20 from the air inlet end, the air suction pipe 20 forms an "L"-shape so as not to hinder the flow of the condensed water 1 which moves downwardly along the inner wall of the condensing tube 10 by gravity.

A condensed water collector for the condensing tube, as shown in FIG. 3, comprises a condensed water vessel 14 which is funnel-shaped and installed beneath the condensing tube 10 and which collects condensed water 1 moving downwardly along the inner wall of condensing tube 10, and a condensed water pipe 15 for transporting condensed water 1 collected in condensed water vessel 14 to the analyzing unit. Condensed water vessel 14 can be made of various materials, but it is possible to make it from soft tubing material, or from the same material as condensing tube 10.

In addition, as shown in FIG. 1, the condensed water collector is constructed to include valves 25, 26, 27, 28, 29 that are installed in condensed water pipe 15 to control the opening and closing of condensed water pipe 15. A controller 50 controls valves 25, 26, 27, 28, 29 by applying control signals thereto so as to selectively open or close the valves. Valves 25, 26, 27, 28, 29 may be any type of practical valve, but are, preferably, solenoid valves which are very easy to control. Controller 50 controls the above valves 25, 26, 27, 28, 29, to open and close, one-by-one or in selected groups, in some specific order, such that the condensed water is predictable and/or continuously supplied to the analyzing unit. In this manner, the analyzing unit continuously receives condensed water collected over known time periods, and analyzes for various kinds of water-soluble contaminants.

The condensed water supplier includes an injector loop 35 installed in condensed water pipe 15 connecting the condensed water vessel 14 and the analyzing unit, wherein the condensed water collected in condensed water vessel 14 is accumulated temporarily before being supplied to the analyzing unit. The condensed water supplier also includes a syringe pump 36 for pushing the condensed water accumulated in injector loop 35 in order to supply it to the analyzing unit.

A typical centrifugal pump or a peristaltic pump may be used instead of syringe pump 36. It is, however, difficult to precisely control the supply amount of pressure provided by these pumps, and more particulate and contaminants can be accumulated therein. Therefore, a reciprocating syringe pump, which is a type of positive displacement pump, is installed because it allows relatively exact control for the condensed water supply with little accumulation of contaminants.

In addition, the condensed water supplier can further have a discharge unit in which condensed water collected in the injector loop may be directly discharged without passing through the analyzing unit. The discharge unit comprises a condensed water discharge pipe 43 installed on an outlet of syringe pump 36 for discharging some amount of condensed water from the condensing unit without passing the condensed water through the analyzing unit, and a discharged water container 44 holding the discharged condensed water.

The relative shape and size of each condensing tube 10 and the amount of air drawn by air suction pipe 20 may be optimized depending on the amount of the condensed water present and the kinds of the water-soluble contaminants contained in the air sample. That is, as shown in FIG. 3, the inner diameter (D) of condensing tube 10 is preferably greater than 3 mm considering the surface tension of the condensed water and the flow of the air sample. More preferably, the inner diameter (D) of the condensing tube 10 ranges from between 4 and 10 mm. Further, the thickness of condensing tube 10 (t) is preferably less than 4 mm in order to improve the efficiency of the thermal transfer. More preferably, the thickness of the condensing tube (t) ranges from 0.5 to 2 mm.

The cooling length of condensing tube 10 (L), which is the length that the condensing tube 10 passes through cooling tank 11, is preferably greater than 100 mm such that the air sample may have enough contact time while it passes through condensing tube 10. More preferably, the length (L) ranges from 600 to 1000 mm.

Vacuum pump 22 for drawing the air sample through condensing tube 10, as shown in FIG. 1, will have a capacity of from 1 l to 200 l per minute according to the shape of condensing tube 10. Also, preferably, the above flow meter, or the mass flow controller 21 will have a single capacity of from 1 l to 20 l per minute.

In addition, referring to FIG. 3, the inner diameter of condensed water pipe 15 is preferably 1 to 10 mm according to the amount of condensed water on the inner wall of condensing tube 20, and its thickness is preferably less than 4 mm, i.e., a thickness ranging from 0.5 to 2 mm.

Syringe pump 36, shown in FIG. 1, for supplying condensed water to the analyzing unit will have a capacity of from 0.1 ml to 2 ml per minute.

Using the above system, contaminant concentration is sufficiently high for analysis despite the relatively small amount of condensed water, the bonding of the contaminant particles or water-soluble ion particles to the water. Thus, the condensed water can be directly supplied to the analyzing unit, and effectively used in analysis.

With reference to FIG. 1, the analyzing unit of the present invention is preferably an ion-chromatography, which comprises, a solvent supplier for mixing a solvent with a condensed water sample for measurement of conductivity, a column 39 receiving the condensed water/solvent mixture, hereafter "the test sample," and ion-separating the test sample into specific material groups, a suppressor 40 for suppressing the conductivity of the solvent within the test sample among the specific material groups as separated by column 39, a conductivity meter 41 for analyzing components of the test sample by measuring the conductivity of the specific materials contained in the test sample passing through suppressor 40, and a discharge line for discharging the test sample after passing through conductivity meter 41. The solvent uses a conventional Eluent showing high performance in suppressing the conductivity of ions, yet mixing well within the test sample.

The solvent supplier includes a solvent supply source 37 and a solvent supply pump 38 for supplying solvent to injector loop 35 through a solvent supply pipe. Solvent is mixed with the condensed water while passing through inject loop 35 of the condensed water supplier. Solvent supply source 37 preferably comprises a level sensor (not shown) for sensing the amount of the solvent, and a controller (not shown) determining a fill time for the solvent based on a level signal from the level sensor.

The discharge line of the ion chromatography includes a test sample discharge pipe 42 installed after conductivity meter 41 and discharging the test sample passing through the analysis unit. The test sample is discharged into discharge water container 44 also containing the discharged condensed water discussed above.

The discharged water container 44 includes a level sensor (not shown) for sensing the amount of discharged water, and a controller (not shown) determining the discharge upon receipt of a signal from the level sensor. In the embodiment of the present invention, discharged water container 44 is commonly used for the discharged condensed water, the discharged test sample, and any liquids passing through the system during cleaning of the condensing unit.

In addition, the ion chromatography further comprises a standard solution supplier for supplying a Standard Solution ($SO_4^{2-}$-standard solution 1000 ppm for ion chromatography from U.S. Alltech Corn.) of positive ions and negative ions, as a test solution to be measured for calibration data during the initialization of conductivity meter 41. The standard solution supplier includes a standard solution supply source 34 and a fluid pump for forming fluid pressure for the standard solution to be supplied to injector loop 35 through a standard solution supply pipe.

The standard solution supply source 34 is constructed such that a plurality of supply tanks are simultaneously connected to the standard solution supply pipe in order to provide various kinds of the standard solution. Three standard solutions are contemplated in one embodiment of the present invention as shown in FIG. 1. Valves 31, 32, 33 are provided on each of the standard solution supply pipes connected to the standard solution supply source 34 in order to selectively open and close the standard solution supply pipes. Further, controller 50 controls the valves 31, 32, 33 in order to selectively open and close the standard solution supply pipes connected to the standard solution supply source 34 by applying control signals to the valves 31, 32, 33.

The fluid pump commonly uses syringe pump 36 of the condensed water supplier for supplying the condensed water tube to the analyzing unit. Syringe pump 36 thus receives condensed water from condensed water pipe 15 and receives a standard solution from standard solution supply source 34 via a 3-way valve 30. The 3-way valve 30 receives a control signal from controller 50 so that either condensed water or standard solution is selectively supplied to the analyzing unit.

The condensed water or the standard solution passing through the 3-way valve 30 is accumulated temporarily in injector loop 35 and is then supplied to suppressor 40 via column 39 by operation of syringe pump 36. As mentioned, column 39 functions to ion-separate a specific sample into specific material groups. In addition, suppressor 40 reduces the conductivity of the Eluent, and increases the conductivity of the condensed water, test sample ions so as to increase the conductivity difference between the Eluent and the test sample, thus improving sensitivity of conductivity meter 41. Suppressor 40 is commercially well-known to those skilled in the art, and a detailed description will thus be omitted.

Conductivity meter 41 of the analyzing unit includes user defined functionality to calculate various data and a display (not shown) displaying results. Typically, this functionality can calculate the concentration of water-soluble contaminants in the air sample by converting the measured conductivity of the sample into a concentration figure, as defined by a comparison with the known conductivity and concentration value of the standard solution. It is then a relatively simple matter to multiply this figure by an amount figure of the test sample induced through the conductivity meter and the absorption rate for the water-soluble contaminants in the air sample.

Thereafter, by using a capture zone ratio for the inside of condensing tube(s) 10 and the ion-concentration, $C_{ion}$ (ppb), of the water-soluble contaminants measured by analyzing the condensed water gas concentration, $C_{gas}$(pptv) of the water-soluble contaminants in the air is achieved by the Equation (1) as follows:

$$C_{gas} = k \times (24.123) \times n \times (C_{ion}/m_w) \quad (1)$$

where k=correction constant (1-capture zone's ratio)
n=absolute moisture content in the volume of 1 m³ room
$m_w$=molecular weight of analysis gas.

Figure 4:
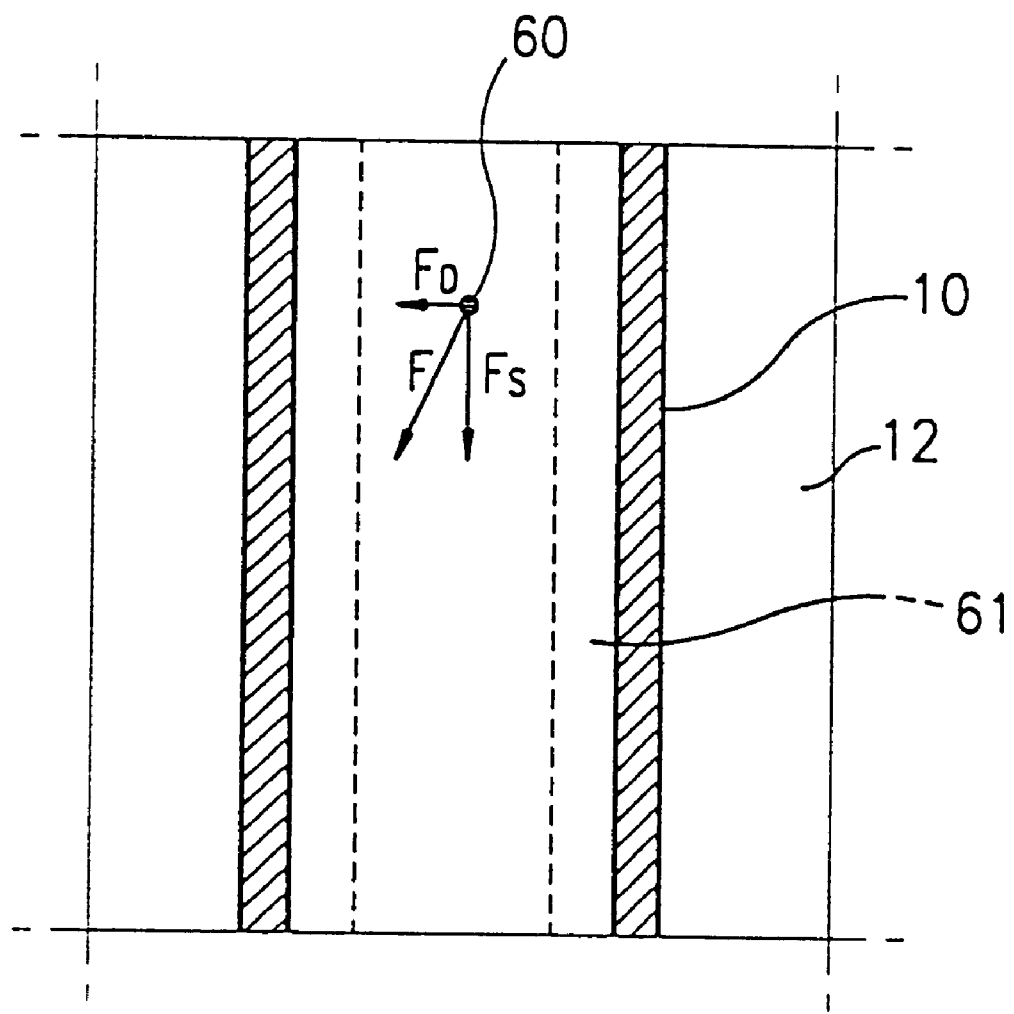
FIG. 4 is a representation showing the force applied to a gas molecule inside the condensing tube of FIG. 3.

FIG. 4 illustrates the capture zone of condensing tube 10 containing a gas molecule 60 influenced by two forces: diffusion ($F_D$) and suction ($F_S$). Diffusion $F_D$ is a force normally diffusing gas molecules toward the inner wall of condensing tube 10, and suction $F_S$ is a force produced by the drawing of the air sample through the condensing tube 10. The gas molecule is actually subject to the sum of these two forces (F), and proceeds downwardly towards the inner wall of condensing tube 10. Then, the gas molecule is captured as condensed water in a capture zone 61 proximate the inner wall of condensing tube 10, i.e., the region in which water vapor inside the reference air is cooled to saturation. Thus, water vapor gas molecules are captured and adhere to the inner wall of condensing tube 10.

Here, Mass Diffusivity (A through B) of gas molecules 60 can be described as Equation (2), wherein $D_{AB}$ is expressed in cm² per sec, and $$D_{AB} = \{0.001858 T^{3/2}(1/M_A + 1/M_B)^{1/2}\} \text{ divided by}(P\sigma_{AB}^2 \Omega_D)$$

where T=absolute temperature (K)
MA, MB=molecular weight of A and B
P=absolute pressure (atm)
AB=collision diameter
D=collision integral for molecular diffusion The collision diameter ($\sigma_{AB}$) can be found by the Equation (3).

$$\sigma_{AB} = (\sigma_A + \sigma_B)/2 \quad (3)$$

The collision integral for molecular diffusion ($\Omega_D$) can be achieved by the Equation (4) and Lennard-Jones constants table.

$$\epsilon_{AB}/k = \sqrt{(\epsilon_A/k)(\epsilon_B/k)} \quad (4)$$

where k: Boltzmann constant $1.38 \times 10^{-16}$ ergs/K
σ and ε: Lennard-Jones parameter Mass Diffusivity of the gas molecules ($D_{AB}$) at a specific temperature $T_1$, and a specific pressure $P_1$ can be simplified as follows by Equation (5).

$$D_{AB} \text{ at } T_1 P_1 = D_{AB} \text{ at } T_2 P_2 (P_1/P_2)(T_2/T_1)^{3/2} \times (\Omega_{D,T1})/(\Omega_{D,T2}) \quad (5)$$

From the above equation, the obtained diffusion coefficient of ammonia gas in the air sample at 21° C., 1 atm is 0.211 cm²/sec., and the diffusion rate is 0.259 cm/sec. Air velocity in the condensing tube is about 2 m/sec., and it takes 0.4 sec. to pass through a condensing tube 800 mm in length. Therefore the capture zone is approximately 1.03 mm from the surface of the tube. Capture zone occupies about 34% of the tube. The ratio occupied by the zone 61 can be adjusted by calculation according to a specific analysis gas. Table 1 shows the calculated diffusion coefficients ($D_{AB}$) and correction coefficients (k) between gaseous contaminants.

TABLE 1

Diffusion Coefficients ($D_{AB}$) and Correction Coefficients (k)

| Gas | $\Omega_D$ | $D_{AB}$ (cm²/s) | Correction Coefficient (k) |
|---|---|---|---|
| NH₃ | 1.233 | 0.211 | 0.655 |
| NO | 0.943 | 0.199 | 0.664 |
| F₂ | 0.939 | 0.197 | 0.666 |
| SO₂ | 1.113 | 0.123 | 0.736 |
| Cl₂ | 1.102 | 0.119 | 0.741 |
| Br₂ | 1.208 | 0.098 | 0.765 |

The capture zone 61 on the inner wall of condensing tube 10 can be variously formed according to the kinds of the gases in the air sample, the absorption velocity of the air sample, the shape of the condensing tube, temperature, and pressure. Using the above equations, it is possible to optimize the absorption rate of the air and the shape of the condensing tube according to the kinds of the gases.

Conductivity meter 41 of the analyzing unit further comprises a memory device (not shown) containing a data-base for the measured values so as to check the measured values when necessary. The analyzing unit of the present invention may also comprise a particle counter 70 for measuring the particles in the air sample so as to check the state of the air sample introduced into the condensing unit. Further, a thermometer, hygrometer, pressure gauge (not shown) are provided in order to measure temperature, humidity of the reference air induced into condensing unit.

In addition, the exemplary embodiment of the cleanroom environment analysis system according to the present invention is set for the nominal conditions, i.e., humidity of about 30 to 90%, temperature of about 20 to 40° C., but it is possible to install a supplementary system for adjusting the and temperature and the humidity of the reference air sample when the conditions of the air to be analyzed extend beyond these nominal conditions, or when it is necessary to adjust the amount of the condensed water by controlling the humidity. The supplementary system is conventional, i.e., comprising a heater, humidifier, air cooler, dehumidifier, etc.

In another aspect of the present invention, an analysis method for analyzing a cleanroom environment using the foregoing analysis system, generally comprises the steps of condensing the water-soluble contaminants contained in an air sample by cooling the reference air sample, supplying the condensed water to the analyzing unit; and analyzing the supplied condensed water in the analyzing unit.

The method may include a step of preparing the analyzing unit. That is, initialization data is obtained to establish a baseline in the analyzing unit by supplying a standard solution of positive ions, or negative ions, as a test sample. In this step, controller 50 shown in FIG. 1 controls valves 31, 32, 33 connected to the standard solution supply pipe so as to selectively supply a standard solution to the analyzing unit.

Also, by use of controller 50, syringe pump 36 is controlled so as to supply the standard solution to the analyzing unit simultaneously with the opening of the valves 31, 32, 33. In this manner, a selected standard solution is mixed with Eluent in injector loop 35 so as to be supplied to the analyzing unit, and initialization data for the standard solution is obtained.

The foregoing method may also include a cleaning step performed before the step of condensing in order to prepare the condensing unit. In order to clean out the old condensed water existing inside the condensing unit with new condensed water, a certain amount of the condensed water is drained out of the condensing unit without passing through the analyzing unit. That is, 3-way valve 30 is controlled by the controller 50 so that the standard solution supply pipe is shut, and condensed water pipe 15 is connected to injector loop 35, and then by controlling injector loop 35, condensed water does not go into the analyzing unit, but instead, is passed through the outlet of syringe pump 36. Then, the condensed water is passed to condensed water discharge pipe 43 and drained out into discharged water container 44.

After performing the above step, a step of condensing is carried out so as to supply the condensed water condensed by the condensing unit into the analyzing unit.

The condensing step may be carried out by first cooling down cooling tank 11 to a constant temperature of between 0 and 10° C. using compressor 23 and expander 24 and the associated cooling medium as driven by controller 50. Once cooling tank 11 is properly cooled, a vacuum is formed on the one end of condensing tube 10 by vacuum pump 22 to draw the air sample through condensing tube 10. During this step, the amount of air sample drawn will be controlled by the Mass Flow Controller 21 in order to optimize the velocity of the reference air sample passing through the condensing unit, such that the reference air sample is sufficiently cooled before it is discharged.

The water vapor contained in the reference sample air condenses on the inner wall of condensing tube 10 and drips down into condensed water vessel 14 as shown in FIG. 3. From condensed water vessel 14 the condensed water is supplied into the analyzing unit through condensed water pipe 15 connected to condensed water vessel 14. At this time, each of valves 25, 26, 27, 28, 29 provided on condensed water pipes 15 is opened one by one by controller 50 shown in FIG. 1 so as to continuously supply the condensed water into the analyzing unit. That is, if condensed water is collected in each of the five condensed water vessels during an interval of approximately 10 to 40 min., any one of valves 25, 26, 27, 28, and 29 may be opened so as to supply the condensed water into the analyzing unit. In this manner, reference air samples from the cleanroom may be analyzed continuously. "On-line" analysis of the cleanroom environment is accordingly provided and certain manufacturing steps, time periods, or time varying conditions may be evaluated.

Then, in order to supply the condensed water from condensing tube 10 to the analyzing unit, syringe pump 36 is operated under control of controller 50 and condensed water from a condensing tube having an open valve is supplied to injector loop 35 via condensed water pipe 15. Then, under pressure from syringe pump 36, the condensed water is supplied into the column 39 of the analyzing unit. At this time, the discharge line connected to the outlet of syringe pump 36 is closed, and condensed water is mixed with Eluent, which always flows to the analyzing unit so as to be supplied to column 39. Next, the step of analyzing the condensed water is performed by the analyzing unit. Column 39, receiving a sample of condensed water mixed with the Eluent, ion-separates the sample into specific material groups, and supplies it to the suppressor, which suppresses the conductivity of the Eluent mixed with the condensed water among the separated specific material groups. Conductivity meter 41 measures the conductivity of the specific material contained in the above sample supplied from suppressor 40, wherein the conductivity of the Eluent is suppressed. With the completion of the analysis, the sample and the Eluent are drained out of the analyzing unit. The analyzing unit measures the temperature, pressure, and number of the particles in the reference air sample before the results of the sample analysis are written to the database.

Therefore, according to a cleanroom environment analysis system and method according to the present invention, the time required to capture water-soluble contaminants is greatly reduced, and the efficiency and accuracy of testing are dramatically improved. All this in a real-time "On-line" system which allows time period or manufacturing step related contamination data to be effectively collected.

The foregoing embodiment of the present invention has been given by way of example. One of ordinary skill in the art will understand that various changes, substitutions and alterations can be made hereto without departing from the scope of the invention as defined by the appended claims.

What is claimed is:

1. An environment analysis system for analyzing air in a cleanroom to detect for contaminants in the air which are water-soluble, said system comprising:

at least one vertically extending condenser tube having an open top end through which an air sample extracted from the cleanroom can be introduced into the tube, a side wall having an inner surface past which the air sample will flow downwardly within the tube, and an open bottom end;

cooling means, disposed outside the at least one condenser tube, for cooling the side wall of the at least one condenser tube from the outside thereof to thereby form a condensate of the air sample inside the tube and which flows downwardly along the inner surface of the side wall and drips from the open bottom end of the condenser tube;

vacuum pressure generator means for inducing air into the at least one condenser tube from the open top end thereof and thereby forcing the air to flow downwardly through the condenser tube towards the bottom end thereof;

an analyzing unit capable of analyzing the condensate for water-soluble contaminants; and a condensed water pipe having a respective first end connected to the bottom end of each said at least one condenser tube, and a second end connected to said analyzing unit, whereby condensate dripping from the bottom end of the at least one condenser tube flows to said analyzing unit via said condensed water pipe so that contaminants are detected for in real time.

2. The analysis system of claim 1, wherein said cooling means comprises a tank through which each said at least one condenser tube passes.

3. The analysis system of claim 2, wherein said at least one condenser tube comprises a plurality of parallel condenser tubes.

4. The analysis system of claim 2, wherein each said at least one condenser tube is of glass.

5. The analysis system of claim 1, wherein said cooling means comprises:
- a cooling tank containing a cooling fluid in contact with the outside of each said at least one condenser tube; and
- a compressor, an expander, and a refrigerant line containing a coolant and defining a cooling cycle such that the coolant circulates between the compressor and the expander.

6. The analysis system of claim 5, wherein the cooling fluid is one selected from a group consisting of water and gas.

7. The analysis system of claim 5, wherein the cooling tank comprises a back portion, and a front door assembly mounted to said back portion so as to be openable and closable thereover, and wherein each said at least one condenser tube is detachably mounted to said tank such that when the front door assembly is opened, each said at least one condenser tube may be removed from the cooling tank.

8. The analysis system of claim 5, and further comprising a controller driving the compressor at such a cycle that the temperature of the inner surface of each said at least one condenser is maintained within a range of from 0° C. to 10° C.

9. The analysis system of claim 1, wherein the vacuum pressure generator means comprises:
- a respective air suction pipe having one end extending into the open bottom end of a said condenser tube, and
- a vacuum pump attached to another end of the air suction pipe and creating a vacuum in the air suction pipe which draws air through the condenser tube into which the air suction pipe extends.

10. The analysis system of claim 9, wherein the one end of the air suction pipe extends upwardly into the bottom end of the condenser tube and is spaced in its entirety from the inner surface of the side wall of the condenser tube.

11. The analysis system of claim 10, wherein the vacuum pressure generator means further comprises a mass flow controller connected to the air suction pipe and defining the volume of the air drawn through the condenser tube into which the air suction pipe extends.

12. The analysis system of claim 1, collector comprises:
- and further comprising a condensed water vessel having the shape of a funnel and mounted beneath the condenser tube to capture condensate dripping from the condenser tube; and
- wherein said condensed water pipe is connected to said condensed water vessel such that condensate collected in the condensed water vessel is transported to the analyzing unit.

13. The analysis system of claim 12, and further comprising a valve disposed in the condensed water pipe, and a controller selectively opening and closing the valve.

14. The analysis system of claim 3, and further comprising:
- a plurality of condensed water vessels, each having the shape of a funnel, and each being mounted beneath a respective said condenser tube to capture condensate dripping from the respective condenser tube,
- said condensed water pipe being connected to each of said water vessels such that condensate collected in each of said condensed water vessels is transported to the analyzing unit;
- a controller; and
- a plurality of valves disposed in the condensed water pipe, the controller being operatively connected to said valves so as to selectively open and close each one of the valves, and each of the valves being associated with a respective one of the condenser tubes, such that the selective opening and closing of the valves regulates the transport of condensate from the associated condenser tubes to the analyzing unit.

15. The analysis system of claim 14, wherein each one of the plurality of valves comprises a solenoid valve.

16. The analysis system of claim 12, and further comprising:
- an injector loop disposed in the condensed water pipe such that condensate collected in the condensed water vessel is temporarily accumulated in the injector loop before being supplied to the analyzing unit; and
- a fluid pump providing pressure to the condensate accumulated in the injector loop.

17. The analysis system of claim 16, wherein the fluid pump is a positive displacement syringe pump having a pump capacity of from 0.1 to 2 l per minute.

18. The analysis system of claim 16, and further comprising a discharge pipe connected to the injector loop and bypassing the analyzing unit such that condensate accumulated in the injector loop can be discharged from the injector loop without passing through the analyzing unit.

19. The analysis system of claim 18,
and further comprising a discharged water container connected to said condensed water discharge pipe so as to receive the condensate from the condensed water discharge pipe.

20. The analysis system of claim 19,
and further comprising a level sensor sensing the amount of condensate in the discharge water container; and
- a controller operatively connected to said level sensor so as to receive a signal from the level sensor indicative of the level of condensate in said discharge water container.

21. The analysis system of claim 1, wherein the analyzing unit is an ion chromatography device.

22. The analysis system of claim 21, wherein the ion chromatography device comprises:
- a solvent supply source connected to said condensed water pipe, such that a solvent mixes with the condensate to form a test sample;
- an ion-seperation column connected to said condensed water pipe downstream of said solvent supply source so as to receive the test sample and ion-separated the test sample into specific material groups;
- a suppressor for suppredding the coductivity of the solvent is the test sample among the specific material groups separated in the column;
- a conductivity meter connected to suppressor and to aid ion-separation column so as to measure the conductivity of the specific material groups; and
- a discharge line extending form the conductivity meter for discharging the test sample passing through the conductivity meter.

23. The analysis system of claim 22, supplier further comprises:

and further comprising a solvent supply pump connected in-line between the solvent supply source and said injector loop so as to pump the solvent from the solvent supply source to the injector loop.

24. The analysis system of claim 22, wherein the ion chromatography device further comprises a standard solution supplier, including at least one source of a standard solution connected to said conductivity meter, so as to supply a standard solution of ions to the conductivity meter used to calibrate the conductivity meter.

25. The analysis system of claim 22, wherein the conductivity meter of the analyzing unit comprises a user defined functional tool adapted to calculate concentration of water-soluble contaminants in the air sample as a product of measured values.

26. The analysis system of claim 25, wherein the conductivity meter further comprises a memory storing the measured values.

27. The analysis system of claim 1, further comprising
a particle counter for counting particles contained in the air sample;
a hygrometer for measuring the humidity of the air sample;
a thermometer for measuring the temperature of the air sample; and
a pressure gauge for measuring the pressure of the air sample.

28. An analysis method for analyzing air in a cleanroom to detect for contaminants in the air which are water-soluble, comprising the steps of:
placing at least one vertically extending condenser tube in communication with the environment of the cleanroom, the condenser tube having an open top end through which an air sample from the cleanroom can be introduced into the tube, a side wall having an inner surface, and an open bottom end;
creating a pressure differential in which pressure within the condenser tube at the bottom end of the condenser tube is less than that at the top end of the tube to thereby induce a sample of air from the cleanroom into the tube and force the air to flow downwardly in the tube toward the bottom end thereof;
cooling the side wall of the condenser tube from the outside thereof to produce within the tube condensate containing water-soluble contaminants present in the air sample, whereby the condensate flows downwardly along the inner wall surface and drips out the open bottom end of the tube; and
collecting the condensate dripping from the open bottom end of each said at least one condenser tube and supplying the collected condensate to an analyzing unit capable of detecting the presence of water-soluble contaminants in the condensate.

29. The analysis method of claim 28, further comprising a step of:
controlling the pressure differential such that the air sample is drawn through the tube at a velocity calculated to produce condensate in a predetermined capture zone within the tube.

30. The analysis method of the claim 28, further comprising steps of:
mixing a solvent with at least a portion of the condensate to form a test sample; and
feeding the test sample to the analyzing unit.

31. The analysis method of claim 28, further comprising steps of:
prior to cooling the condenser tube, cleaning the condenser tube by directing condensate as cleaning water through the tube toward the bottom end thereof in order to remove water existing inside the condenser tube; and
diverting the cleaning water from passing through the analyzing unit once the cleaning water has flowed out of the condenser tube.

32. The analysis method of the claim 29, further comprising steps of:
measuring temperature, humidity, and pressure of the air sample and measuring contaminant particles in the air sample before the air sample is drawn into the condenser tube.

33. The analysis method of claim 28, wherein the supplying of the condensate comprises pumping the condensate dripping form the at least one condenser tube to the analyzing unit.

* * * * *